United States Patent

Jacobsen et al.

Patent Number: 5,141,493
Date of Patent: Aug. 25, 1992

[54] PERITONEAL DIALYSIS SYSTEM

[75] Inventors: Stephen C. Jacobsen; Barry K. Hanover; Robert L. Stephen, all of Salt Lake City, Utah

[73] Assignee: Sarcos Group, Salt Lake City, Utah

[21] Appl. No.: 470,978

[22] Filed: Jan. 26, 1990

[51] Int. Cl.⁵ .............................................. A61M 1/28
[52] U.S. Cl. ........................................ 604/29; 604/30; 604/28; 210/646; 210/104; 210/321.71
[58] Field of Search ........................ 604/4-6, 604/27-30; 210/321.3, 646

[56] References Cited

U.S. PATENT DOCUMENTS

| | | | |
|---|---|---|---|
| 4,190,047 | 2/1980 | Jacobsen et al. | 604/29 X |
| 4,412,917 | 11/1983 | Ahjopalo | 604/29 X |
| 4,586,920 | 5/1986 | Peabody | 604/29 |
| 4,618,343 | 10/1986 | Polaschegg | 604/29 |

Primary Examiner—Robert A. Hafer
Assistant Examiner—Kerry Owens
Attorney, Agent, or Firm—Thorpe, North & Western

[57] ABSTRACT

A peritoneal dialysis system is disclosed for administering substantially sterile dialysate to the peritoneal cavity of a patient. The system includes a dialyzer for passing a primary solution and a secondary solution therethrough to enabale removal of waste products from the primary solution to the secondary solution, and a primary circuit for selectively circulating a primary solution through the dialyzer. Connecting conduits or tubing is provided for selectively carrying primary solution from the primary circuit to the peritoneal cavity of the patient and for selectively withdrawing at least some of the solution from the peritoneal cavity back into the primary circuit. A pump is disposed in the primary circuit for causing primary solution to circulate in the primary circuit independently of transfer of primary solution between the primary circuit and the peritoneal cavity of the patient. A secondary circuit is coupled to the dialyzer for supplying a secondary solution thereto and for carrying secondary solution from the dialyzer. A supply source of primary solution is coupled to the primary circuit to initially charge the circuit, and a supply source of secondary solution is coupled to the secondary circuit to continually supply secondary solution thereto.

34 Claims, 2 Drawing Sheets

PERITONEAL DIALYSIS SYSTEM

BACKGROUND OF THE INVENTION

This invention relates to a simple, efficient and flexible peritoneal dialysis system utilizing a primary circuit of sterile dialysate solution and a secondary circuit of non-sterile dialysate solution.

Two conventional artificial approaches to treating blood poisoning as well as end stage renal disease and acute renal failure are hemodialysis and peritoneal dialysis. Both approaches serve to remove metabolic waste products (dialysis) and excess water (ultrafiltration) from the blood of a patient. In hemodialysis a portion of a patient's blood is circulated through a dialysis cell in which the patient's blood passes on one side of a semi-permeable membrane and a dialysate solution on the other side. The semi-permeable membrane passes the metabolic waste products and excess water from the patient's blood to the dialysate solution. Among the problems or disadvantages in hemodialysis are the need to chemically condition the blood against unwanted clotting and the need for removing blood from the body in an extracorporeal circuit to enable treating the blood. This latter need can give rise to blood component damage and blood pressure instability during the time the blood is out of the body.

In peritoneal dialysis, sterile dialysate solution is introduced into the peritoneal cavity of a patient, allowed to remain there for some predetermined period of time, and then removed (or at least a portion thereof) from the cavity. This alternate introduction and removal of dialysate solution is repeated for a sufficient length of time to remove metabolic waste products and excess water from the patient's blood circulating through the peritoneal membrane.

Although peritoneal dialysis simplifies or eliminates some of the problems presented with hemodialysis, a number of disadvantages still exist including the problem and danger of peritonitis, a lower efficacy than hemodialysis which therefore requires a longer treatment or process time with large volumes of solution, and the high cost of commercially prepared dialysate solution. This high cost arises from the need to use sterile dialysate solution to preclude peritonitis and the limited number of sources of commercially prepared dialysate solution.

An additional concern with currently available techniques for carrying out peritoneal dialysis is the need to maintain the proper blood chemistry balance for each patient treated where each patient may react differently to the dialysis treatment. That is, it is necessary to maintain a certain sodium electrolyte concentration which, during the dialysis process, tends to get out of balance because of the removal of water (ultrafiltration). When water is removed from the body by ultrafiltration, more water proportionally tends to be removed than does sodium, leaving an out of balance, higher-than-desired concentration of sodium in the water remaining in the body. As a consequence, as the dialysis process proceeds, it would be desirable to be able to carefully control the proportions of osmotic agent and sodium supplied back to the body via dialysate solution, and allow for adjustments, to ensure the maintenance of the proper concentration of sodium remaining in the body. Applicants are unaware of any systems presently available for doing this.

In U.S. Pat. No. 4,618,343, peritoneal dialysis apparatus is disclosed which utilizes a single bore catheter connected to a first circuit for delivering sterile dialysis solution from the first circuit to the peritoneal cavity of a patient and for removing dialysis solution from the cavity and returning it to the first circuit. The first circuit is coupled by way of a dialyzer to a second circuit which is operated in a single-pass mode to remove, through the dialyzer, metabolic waste products from the dialysis solution circulating in the first circuit. A so-called balancing chamber group is provided in the second circuit to control ultrafiltration. This balancing chamber group is connected to the inlet of the first dialyzer, and an outlet of the first dialyzer is connected back to the balancing chamber group.

Another two-circuit dialyzer system is disclosed in U.S. Pat. No. 4,190,047 in which a primary circuit is coupled by way of a catheter to the patient and by way of a dialyzer to a recirculating secondary circuit.

SUMMARY OF THE INVENTION

It is an object of the invention to provide a simple, efficient, easy to use and economical single-pass peritoneal dialysis system in which sterile dialysate solution is intermittently pumped from a primary circuit into and out of a patient, and is maintained sterile by way of a secondary circuit coupled via a dialyzer to the primary circuit.

It is another object of the invention to provide such a dialysis system in which application of dialysate solution to and from the patient from the primary circuit and circulation of dialysate solution in the primary circuit may be carried out selectively and independently of one another.

It is an additional object of the invention to provide such a dialysis system in which the flow rates of dialysate solution in the primary and secondary circuits may be independently controlled to improve the efficiency and economy of the operation of the system.

It is also an object of the invention to provide such a dialysis system in which the electrolyte and osmotic agent concentration in the dialysate solution may be independently and selectively controlled and adjusted as required for the dialysis procedure.

The above and other objects of the invention are realized in a specific illustrative embodiment of a peritoneal dialysis system for administering substantially sterile dialysate solution to the peritoneal cavity of a patient, said system including a dialyzer for passing a primary dialysate solution and a secondary dialysate solution therethrough to enable removal of waste products from the primary solution to the secondary solution, and a primary circuit for selectively circulating a primary dialysate solution through the dialyzer, a delivery or connection element for selectively carrying primary solution from the primary circuit to the peritoneal cavity and withdrawing at least some solution from the peritoneal cavity into the primary circuit, all independently of circulation of primary solution in the primary circuit. A secondary circuit is also provided for supplying a secondary dialysate solution to the dialyzer and for carrying secondary solution from the dialyzer. The system also includes apparatus for initially supplying sterile primary dialysate solution to the primary circuit, for supplying secondary dialysate solution to the secondary circuit, and for receiving secondary solution from the secondary circuit. With the independence of (1) circulation of primary solution in the primary circuit, and (2) from delivery of primary solution to and removal of primary solution from the patient, the speed and efficiency of the dialysis procedure can be better controlled and maximized. The secondary solution and dialyzer serves to maintain the sterility of the primary solution so that the same solution can be circulated in the primary circuit without the need for a continuous supply of fresh sterile dialysate solution.

BRIEF DESCRIPTION OF THE DRAWINGS

The above and other objects, features and advantages of the invention will become apparent from a consideration of the following detailed description presented in connection with the accompanying drawings in which FIGS. 1A and 1B, with FIG. 1B positioned to the left of FIG. 1A, show a schematic of a two-circuit peritoneal dialysis system made in accordance with the principles of the present invention.

DETAILED DESCRIPTION

Figure 1A:
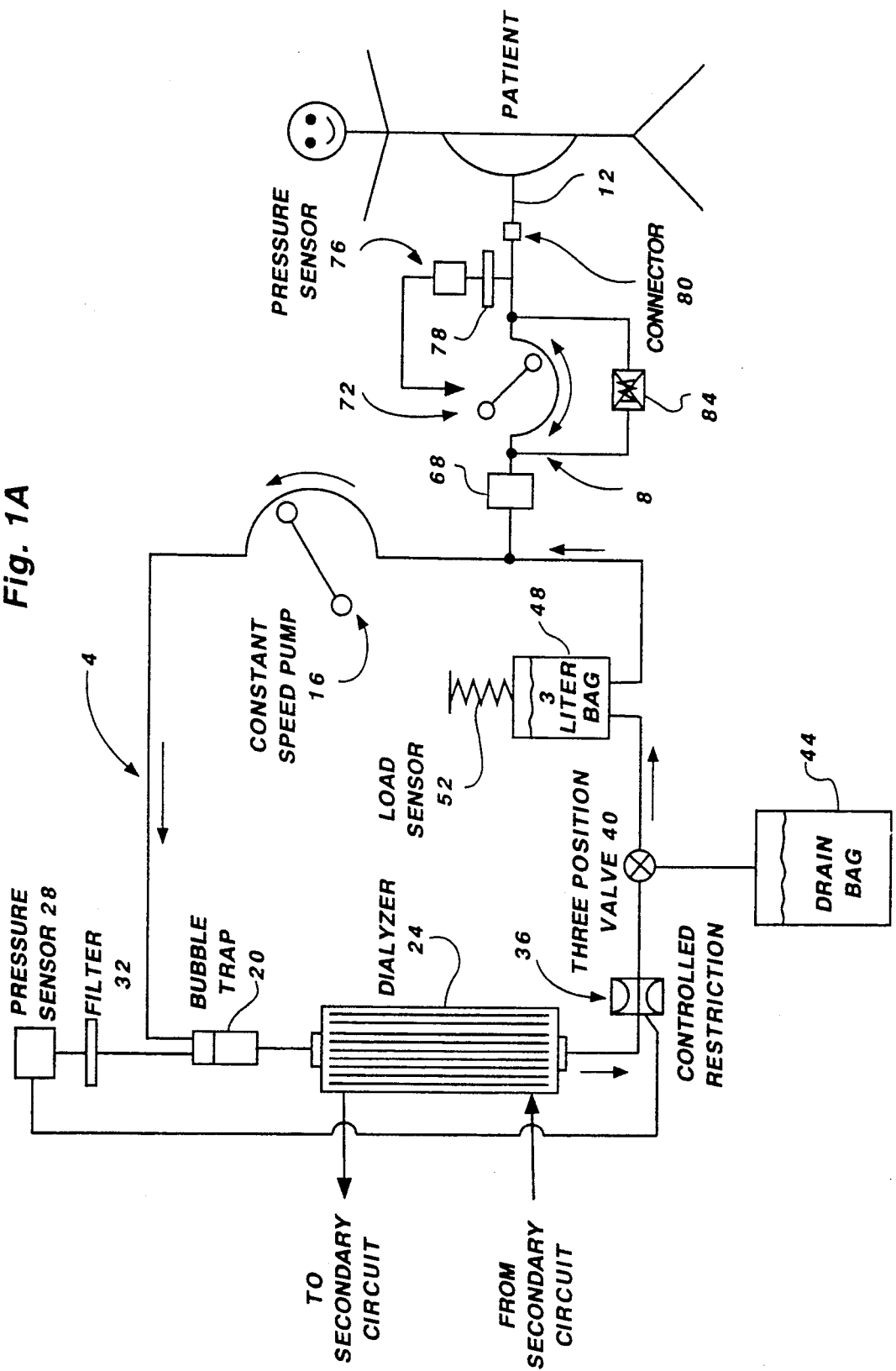

Referring to FIG. 1A, there is shown a primary dialysate solution circuit 4 comprised of ducts, tubing or pipes for carrying a sterile dialysate solution and making it available for delivery via connector or delivery tubing 8 to a catheter 12 inserted into the peritoneal cavity of a patient 16. The primary circuit 4 includes a setable constant speed pump 16 connected by tubing to a conventional bubble trap device 20 which, in turn, is connected by tubing to a conventional dialyzer 24. A fluid pressure sensor 28 is coupled by way of a filter 32 also to the bubble trap device 20, as will be discussed in greater detail later. The dialyzer 24 is also coupled into a secondary dialysate solution circuit shown in FIG. 1B.

The primary circuit 4 also includes a variable position pinch valve 36 for restricting the flow of primary dialysate solution in the circuit under controlled conditions. A three-position valve 40 couples the primary circuit 4 to a drain receptacle or bag 44. The valve 40 may be disposed to either direct dialysate solution from the primary circuit 4 into the drain bag 44 or to allow the solution to circulate in the circuit.

Finally, a solution container 48 is coupled into the primary circuit 4 to receive solution therefrom and to deliver solution back into the circuit. The container 48 also serves as the initial source of solution for the primary circuit and patient, and would be inserted in place at the beginning of the dialysis procedure. A load sensor 52, which might illustratively be a weight scale, is connected to the container 48 for measuring the amount of solution (weight, volume, etc.) in the container 48. It should be understood that an alternate source of dialysate solution, besides that in container 48, could be coupled into the primary circuit 4.

Disposed in the connector tubing 8 is a filter 68, and a reversible, variable speed pump 72. A solution pressure sensor 76 is also coupled by way of a filter 78 (for protecting the sensor) into the connector tubing 8 to produce a signal when the pressure in the connector tubing exceeds or falls below a certain range, (this to be discussed later). The connector tubing 8 is coupled by a connector 80 to the catheter 12. A pressure relief bypass valve 84 is coupled in parallel with the pump 72 to operate and bypass the pump if the pressure drop across the pump exceeds a certain level. In effect, valve 84 serves as a backup to sensor 76.

Illustrative steps in carrying out peritoneal dialysis on the patient 16 include first inserting a container 48 of sterile dialysate solution into the circuit 4, and then operating pump 16 to draw solution from the container and move it into the circuit 4. While this is taking place, air which may be contained in the circuit tubing is forced out the bubble trap 20, and solution is pumped into and through the dialyzer 24. Since the dialyzer 24 typically would be a new, previously unused dialyzer, it might contain contaminants, particulate matter, and chemical residues remaining, for example, from sterilization processes carried out during the manufacture of the dialyzer. These contaminants, particulate matter, etc. are carried by the initial surge of solution through the valve 40 and into the drain bag 44. After "flushing" any air contained in the circuit out through the bubble trap and the contaminants, particulate matter, etc. out of the dialyzer 24, the valve 40 is operated to prevent further flow of solution to the drain bag so that subsequent pumping by the pump 16 causes the solution to move into the rest of the circuit 4 and then recirculate.

The dialysate solution is then pumped from the primary circuit 4 via the pump 72 into the patient 16. The patient's peritoneal cavity is substantially filled with sterile dialysate solution, for an adult typically from about 1.5 to 2.5 liters. The dialysate solution supplied to the patient may be allowed to reside in the peritoneal cavity for some predetermined period of time after which at least a portion of the solution would be pumped from the patient back into the primary circuit 4; or the solution supplied to the patient could be successively pumped into and then pumped out of the peritoneal cavity so that "fresh" dialysate solution would be substantially continuously maintained in contact with the peritoneum. In this last-described mode of operation, the pump 72 is alternately operated in the forward direction, then the reverse direction, then the forward direction, etc., to develop a reciprocating action of supplying solution to and removing solution form the peritoneal cavity of the patient 16.

While the dialysate solution is being reciprocated into and out of the peritoneal cavity of the patient 16, the solution in the primary circuit 4 is being circulated by the constant speed pump 16 through the dialyzer 24 to thereby regenerate and purify the dialysate solution applied to and removed from the patient 16. Thus, unlike other currently available peritoneal dialyzer systems, the system of FIG. 1A (and 1B) can be operated to simultaneously reciprocate dialysate solution into and out of the patient and purify and regenerate such solution by circulating it in the primary circuit 4. This allows for better mixing of solution in the peritoneal cavity and thus more efficient dialysis. By utilizing the primary circuit 4 in conjunction with the secondary circuit of FIG. 1B, substantially less fresh sterile dialysate solution is used in carrying out a dialysis procedure, for example, three liters of dialysate solution versus forty liters if there were no regeneration and purification of the primary solution.

The function of the pinch valve 36 is to allow building up pressure against the flow of primary solution in the primary circuit 4 so that such solution is under pressure in the dialyzer 24. This pressure tends to force water from the primary solution through the membrane in the dialyzer to the secondary solution flowing in the secondary circuit. In order to maintain a certain rate of flow of water from the primary circuit to the secondary circuit, a certain predetermined pressure (for the dialyzer membrane being used) needs to be maintained in the dialyzer 24. The pressure sensor 28 provides one measure of this pressure (also could measure a "transmembrane" pressure between sensor 28 and pressure sensor 196 (FIG. 1B)), and signals the pinch valve 36 to operate to maintain the pressure at the predetermined level. (The reason for passing water from the primary circuit 4 to the secondary circuit of FIG. 1B is to discharge excess water drawn from the patient 16 into the primary circuit [by osmatic action]).

The container 48 and load sensor 52 allow the user of the system to maintain a measure of the amount of dialysate solution flowing in the primary circuit 4 and thus a measure of the amount of solution reciprocating in and out of the patient 16 and cleansed in the primary circuit.

The pressure sensor 76 determines the pressure of dialysate solution entering and leaving the patient 16 and in effect monitors the solution pressure in catheter 12 to ensure that solution is properly supplied to and removed from the patient. For example, if the measured pressure rises above a certain level indicating a possible blockage or kink in the catheter 12, then the pressure sensor 76 could be arranged to signal the pump 72 to cause it to stop. On the other hand, if the measured pressure dropped below some predetermined level, indicating blockage in the catheter 12, such as by sucking against tissue, the pump 72 could be caused to reverse or stop.

Figure 1B:
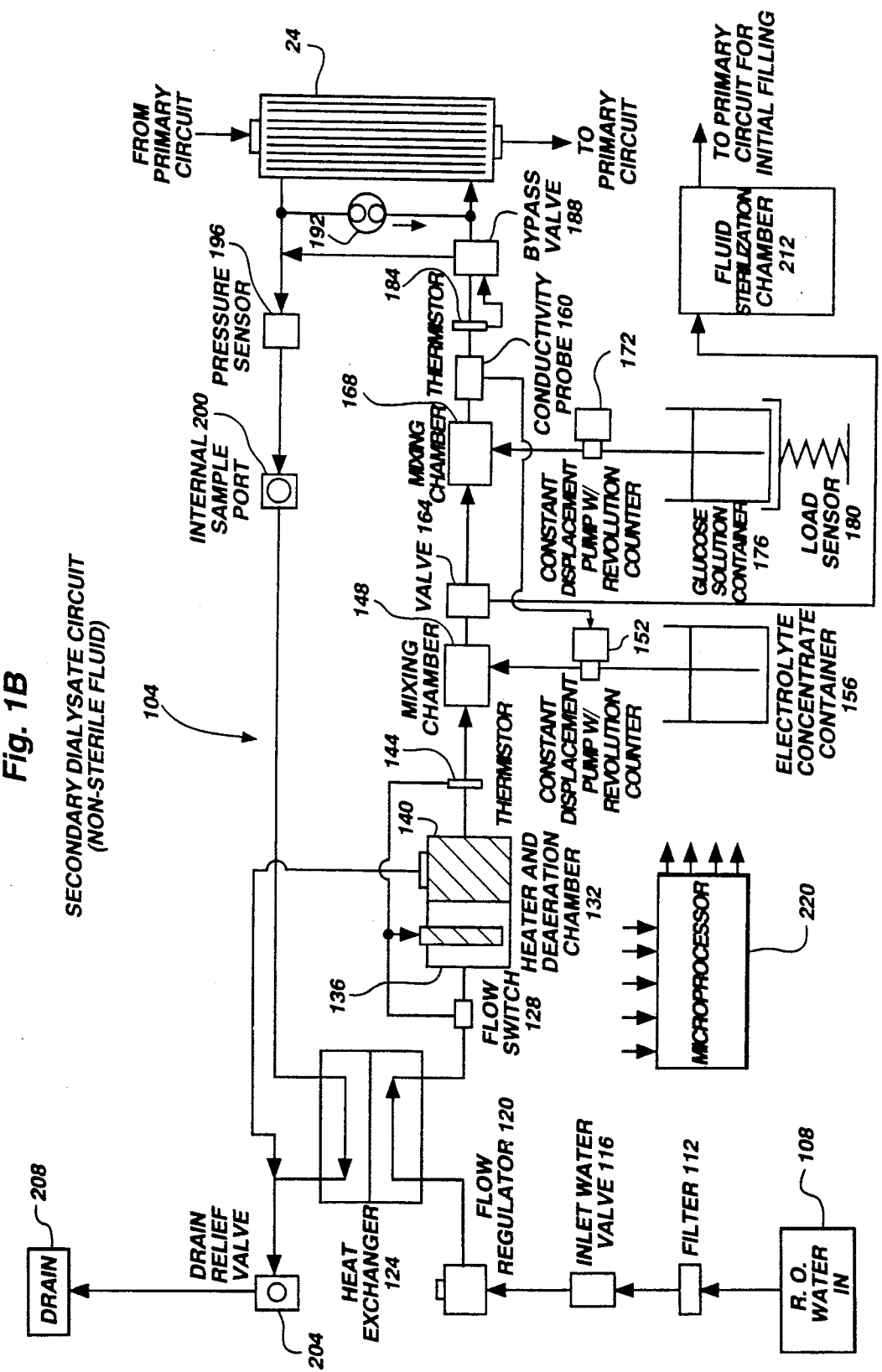

Referring to FIG. 1B, there is shown a secondary circuit 104 for supplying non-sterile dialysate solution to the dialyzer 24. The secondary circuit 104 includes a source of non-sterile but purified water 108 which is supplied, under pressure, to a filter 112 and then to an inlet valve 116 and a flow regulator 120. The flow regulator 120 reduces and controls the pressure at which water from the source 108 is supplied to the rest of the secondary circuit 104.

The water flows from the flow regulator 120 to a heat exchanger 124 where heat from used solution which has already passed through the dialyzer 24 is transferred to the water just received from the flow regulator. From the heat exchanger 124, the water flows via a flow switch 128 to a heater and deaeration chamber 132. This chamber includes a heater element 136 for further heating the water and a deaeration section 140 which removes bubbles from the water and either passes them to the exit part of the secondary circuit 104, or into the atmosphere. The flow switch 128 operates to shut off the heater 136 if the flow rate of the water falls below some predetermined level—to prevent the heater from overheating and becoming damaged. A thermistor 144 is connected to the outlet side of the heater and deaeration chamber 132 for monitoring the temperature of the water and for signalling the heater element 136 to either increase or decrease the temperature of the water to whatever temperature is desired, typically 39 to 41 degrees centigrade.

A mixing chamber 148 is coupled into the secondary circuit to receive water flowing from the heater and deaeration chamber 132 and for receiving an electrolyte solution pumped thereinto by a constant displacement pump 152 from an electrolyte concentrate container 156. The pump 152 responds to a signal from a conductivity probe or sensor 160 which detects the electrolyte concentration in the solution flowing through the secondary circuit 104; if the electrolyte concentration is less than a certain desired level, the probe 160 signals the pump 152 to pump more electrolyte solution to the mixing chamber 148, and vice versa. The mixing chamber 148 mixes the electrolyte solution with the water and passes it via a valve 164 to another mixing chamber 168.

The mixing chamber 168 mixes the solution received from mixing chamber 148 with an osmotic agent solution, in this case a glucose solution, pumped thereto by a constant displacement pump 172 from a glucose solution container 176. The container 76 is mounted on or coupled to a load sensor 180 for measuring the quantity (either volume or weight) of solution in the container. The load sensor 180 is provided primarily to monitor withdrawal of glucose solution from the container 176 to make sure that in fact solution is being withdrawn and supplied to the secondary circuit. If it is not, the load sensor 180 would provide a signal so that the user of the system was made aware that glucose solution was not being properly supplied.

Another thermistor 184 is disposed in the secondary circuit 104 just after the conductivity probe 160 to again monitor the temperature of the solution just before the dialyzer 24 so that if the temperature moves outside a certain preselected range, the thermistor will operate a bypass valve 188 to direct secondary circuit solution around the dialyzer 24. The bypass valve 188 might also be operated to shunt secondary circuit solution past the dialyzer until the correct conductivity is reached. The bypass valve 188 simply shunts the solution to the secondary circuit outlet of the dialyzer 24 as shown.

Another bypass path, with a pump 192 is provided in parallel with the dialyzer 24 to allow for recirculating secondary solution from the outlet of the dialyzer back to the inlet, for example, to conserve secondary solution or increase the flow rate (removal) efficiency. The pump 192 would simply be turned on to provide for recirculating the secondary solution or turned off to stop such recirculation as desired.

From the dialyzer 24, the secondary solution flow past a pressure sensor 196 and an internal sample port outlet 200 to the heat exchanger 124. The pressure sensor 196 is provided to detect any blockage which may occur in the secondary circuit 104 (and then provide a signal to alert the user of the system) and to provide for measuring a "transmembrane" pressure (pressure from the primary circuit through the dialyzer to the secondary circuit). The internal sample port outlet 200 simply allows for withdrawing samples of solution from the secondary circuit for testing purposes.

After any residual heat in the secondary solution is withdrawn by the heat exchanger 124, the solution flows via a drain relief valve 204 to a drain or drain receptacle 208.

The flow rate of the secondary solution in the secondary circuit 104 may be controlled by appropriate setting of the flow regulator 120, and this flow rate may be set relative to the flow rate in the primary circuit to optimize removal of waste products from the primary solution to the secondary solution. It should be noted that the flow in the dialyzer 24 of the primary solution and secondary solution are in a counter current mode which better facilitates the exchange of waste products and water from the primary solution to the secondary solution.

The supply of electrolyte and glucose to the secondary circuit may be independently controlled to maintain the appropriate electrolyte concentration in the blood of the patient. As is well known, glucose solution acts as an osmotic agent to remove fluid from a patient—water moves from the patient through the peritoneum into the dialysate solution being supplied to the patient's peritoneal cavity in an attempt to dilute the glucose concentration. In this manner, the glucose solution may be used to control the fluid being removed from the patient. With removal of fluid from a patient, the electrolyte concentration in the patient's blood is not removed as rapidly and so the electrolyte concentration must be reduced in secondary circuit 104 to maintain the proper electrolyte balance in the patient's blood.

Valve 164 allows for secondary solution to be drained or removed from the secondary circuit 104 to a fluid sterilization chamber 212 where the solution may be sterilized for subsequent supply to the primary circuit, for example, to initially charge or prime the primary circuit. Advantageously, the output of the fluid sterilization chamber 212 would be coupled into container 48 to recharge the container with sterile solution containing electrolyte but not glucose. Thus, before this sterile solution could be used for application to the patient 16, it would be circulated in the primary circuit 4 through the dialyzer 24 a sufficient number of times to bring the glucose concentration to the desired level and then would be available for pumping into the patient's peritoneal cavity.

The pressure, temperature, load flow and conductivity sensors shown in FIGS. 1A and 1B are all coupled directly to an element which is controlled by the sensors depending upon the reading of the sensor. An alternative arrangement to such direct control would be to provide a microprocessor 220 (FIG. 1B) for receiving signals from the various sensors, probes and switches and for producing output control signals for controlling such elements as pumps 16 and 72 of FIG. 1A, pinch valve 36 and three position valve 40 also of FIG. 1A, heater 136 of FIG. 1B, pumps 152, 172 and 192 and valve 188 of FIG. 1B, etc. In particular, the microprocessor 220 could be programmed to receive a certain input setting to control the concentration ratio of electrolyte and glucose and then to operate pumps 152 and 172 in response to this setting and to the conductivity level determined by probe 160, to maintain the desired concentration ratio.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

I claim:

1. A peritoneal dialysis system for administering substantially sterile dialysate to the peritoneal cavity of a patient comprising
   a dialyzer means for passing a primary solution and secondary solution therethrough to enable removal of waste products from the primary solution to the secondary solution,
   primary circuit means for selectively circulating a primary solution through the dialyzer means,
   connection means for selectively carrying, independently of circulation of primary solution in the primary circuit means, primary solution from the primary circuit means to the peritoneal cavity of the patient and for selectively withdrawing at least some solution from the peritoneal cavity of the patient into the primary circuit means,
   means for initially supplying primary solution to the primary circuit means,
   secondary circuit means for supplying a secondary solution to the dialyzer means and for carrying secondary solution from the dialyzer means,
   means for supplying secondary solution to the secondary circuit, and
   means for receiving secondary solution from the secondary circuit.

2. A system as in claim 1 further including a first pump means disposed in the primary circuit means for selectively causing primary solution to circulate in the primary circuit means, and a second pump means disposed in the connection means for selectively pumping primary solution from the primary circuit means to the peritoneal cavity or from the peritoneal cavity to the primary circuit means.

3. A system as in claim 2 wherein said connection means comprises a conduit for coupling the primary circuit to the peritoneal cavity of the patient, and wherein said second pump means comprises a reversible, variable speed pump.

4. A system as in claim 3 further comprising a pressure sensor means for sensing the pressure of the primary solution in the conduit between the second pump means and the peritoneal cavity of a patient, said second pump means being adapted to respond to the pressure sensor means by changing its speeds, when the sensed pressure is outside a certain predetermined range.

5. A system as in claim 2 further comprising filter means disposed in said connection means for capturing certain protein from primary solution flowing from the peritoneal cavity of the patient to the primary circuit, and for releasing previously captured protein into primary solution flowing from the primary circuit to the peritoneal cavity of the patient.

6. A system as in claim 5 wherein said filter means is adapted to capture protein having a molecular weight of about forty thousand or more.

7. A system as in claim 2 further comprising a pressure relief valve means coupled into the connection means in parallel with the second pump means for allowing the flow of primary solution therethrough when the pressure drop across the second pump means exceeds a predetermined level.

8. A system as in claim 2 wherein said first pump means comprises a selectively settable fixed-speed pump.

9. A system as in claim 2 further including
   flow restricting means disposed in the primary circuit means on the exit side of flow of the primary solution through the dialyzer means for selectively and variably restricting the flow of primary solution in the primary circuit in response to pressure indicating signals, and
   pressure sensing means for measuring the pressure of primary solution across the dialyzer means and for supplying pressure indicating signals to the flow restricting means to thereby control the restriction of flow of the primary fluid through the dialyzer means and thus the pressure of the primary solution in the dialyzer means.

10. A system as in claim 9 wherein said flow restricting means and pressure sensing means are adapted to maintain the pressure of primary solution in the dialyzer means at a predetermined level sufficient to force some liquid from the primary solution through the dialyzer means to the secondary solution.

11. A system as in claim 2 further including a drain means coupled to the primary circuit means for receiving primary solution, and valve means coupled in the primary circuit means and to the drain means, and operable to selectively direct the flow of primary solution into the drain means from the primary circuit and to prevent the flow of primary solution into the drain means and allow the flow through the primary circuit.

12. A system as in claim 2 further including
container means disposed in the primary circuit for receiving and releasing primary solution,
means for determining the amount of the primary solution contained in the container means and for producing a first indicating signal when the amount falls below a certain predetermined level, and a second indicating signal when the amount exceeds a second, higher predetermined level, and
wherein said second pump means is coupled to said amount determining means to operate to pump primary solution from the primary circuit and container means to the peritoneal cavity of the patient when said second indicating signal is produced and until said first indicating signal is produced, and to pump solution from the peritoneal cavity of the patient when said first indicating signal is produced and until said second indicating signal is produced.

13. A system as in claim 12 wherein said amount determining means comprises a weighing scale.

14. A system as in claim 12 wherein said amount determining means comprises a solution level detector.

15. A system as in claim 1 further including first pump means disposed in the primary circuit means for causing primary solution to circulate in the primary circuit and through the dialyzer means at a predetermined flow rate, and flow regulator means disposed in the secondary circuit means for causing secondary solution to flow through the secondary circuit and the dialyzer means at a flow rate at least equal to the predetermined flow rate of the primary solution.

16. A system as in claim 1 further including
means coupled into the secondary circuit for selectively supplying a solution of osmotic agent to the second circuit to mix with the secondary solution and flow to the dialyzer means, and
means coupled into the secondary circuit for selectively supplying a solution of electrolytes to the second circuit to mix with the secondary solution and flow to the dialyzer means.

17. A system as in claim 16 wherein said osmotic agent supplying means includes first means for selectively adjusting the rate of supply of osmotic agent solution to the second circuit, and wherein said electrolyte supplying means includes second means for selectively adjusting the rate of supply of electrolytes solution to the second circuit independently of the supply of osmotic agent solution to the second circuit.

18. A system as in claim 17 further including control means coupled to said first means and second means for receiving input information identifying a desired supply rate of osmotic agent solution and a desired supply rate of electrolyte solution, and for causing the first means to adjust the supply rate of osmotic agent solution to the identified desired supply rate and for causing the second means to adjust the supply rate of electrolyte solution to the identified desired supply rate.

19. A system as in claim 16 wherein said osmotic agent supplying means including
a source of osmotic agent, and
means for conveying osmotic agent from the source to the second circuit at a predetermined rate.

20. A system as in claim 19 wherein said conveying means comprises a constant displacement pump.

21. A system as in claim 20 wherein said osmotic agent supplying means further includes means for sensing the amount osmotic agent conveyed from the source to the second circuit.

22. A system as in claim 16 wherein said electrolyte supplying means includes
a source of electrolyte,
pump means for pumping electrolyte from the source to the second circuit at a rate determined by received control signals, and
means for sensing the electrolyte concentration in the second circuit and for supplying control signals to the pump means to increase the rate of pumping when the electrolyte concentration falls below a predetermined range and to decrease the rate of pumping when the electrolyte concentration exceeds said range.

23. A system as in claim 20 wherein said pump means comprises a constant displacement pump.

24. A system as in claim 16 further including an osmotic agent mixing chamber disposed in the second circuit for receiving osmotic agent from the osmotic agent supplying means and for mixing osmotic agent with the secondary solution, and an electrolyte mixing chamber also disposed in the second circuit for receiving electrolyte from the electrolyte supplying means and for mixing electrolyte with the secondary solution.

25. A system as in claim 16 further including a mixing chamber disposed in the second circuit for receiving and mixing together osmotic agent from the osmotic agent supplying means, electrolyte from the electrolyte supplying means, and secondary solution in the second circuit.

26. A system as in claim 1 further including
heater means disposed in the second circuit upstream of the dialyzer means for heating secondary solution in response to a heat signal, and
means disposed in the second circuit downstream of the heater means for detecting the temperature of the secondary solution and for supplying a heat signal to the heater means when the temperature falls below a predetermined level.

27. A system as in claim 26 further including heat exchanger means coupled into the second circuit at both a first location upstream of the heater means and a second location downstream of the dialyzer means for transferring heat from the secondary solution passing through the second location to secondary solution passing through the first location.

28. A system as in claim 1 further including recirculation means coupled into the second circuit at a first location between the secondary solution supplying means and the dialyzer means, and at a second location between the dialyzer means and the secondary solution receiving means for selectively recirculating the secondary solution in the second circuit.

29. A system as in claim 28 wherein said recirculating means comprises a conduit coupled between the first and second locations, and pump means disposed in the conduit for selectively pumping secondary solution through the conduit.

30. A system as in claim 1 further including bypass means coupled into the second circuit in parallel with the dialyzer means for selectively carrying secondary solution to bypass the dialyzer means.

31. A system as in claim 30 wherein said bypass means comprises a bypass conduit coupled into the second circuit in parallel with the dialyzer means, and a valve disposed in the second circuit for selectively directing secondary solution either to the dialyzer means or to the bypass conduit.

32. A system as in claim 1 further including a deaeration means coupled into the second circuit upstream of the dialyzer means for removing gas bubbles from the secondary solution.

33. A system as in claim 32 further including means for conveying gas taken from gas bubbles in the secondary solution from the deaeration means to the secondary solution receiving means.

34. A system as in claim 1 further including
a sterilization chamber for sterilizing secondary solution,
means disposed in the second circuit for selectively directing secondary solution from the second circuit to the sterilization chamber, and
means for selectively delivering sterilized secondary solution from the sterilization chamber to the initial primary solution supplying means.

* * * * *